United States Patent
Ferguson et al.

(10) Patent No.: US 8,906,362 B2
(45) Date of Patent: Dec. 9, 2014

(54) TISSUE ENGINEERED MENISCUS SCAFFOLDS AND METHODS OF USE

(75) Inventors: Cristin M. Ferguson, Clemmons, NC (US); Mark E. Van Dyke, Winston-Salem, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 312 days.

(21) Appl. No.: 13/258,490

(22) PCT Filed: Mar. 23, 2010

(86) PCT No.: PCT/US2010/028313
§ 371 (c)(1),
(2), (4) Date: Nov. 1, 2011

(87) PCT Pub. No.: WO2010/111263
PCT Pub. Date: Sep. 30, 2010

(65) Prior Publication Data
US 2012/0064043 A1 Mar. 15, 2012

Related U.S. Application Data

(60) Provisional application No. 61/162,433, filed on Mar. 23, 2009.

(51) Int. Cl.
*A61L 27/36* (2006.01)
*A61L 27/38* (2006.01)
*A61F 2/08* (2006.01)

(52) U.S. Cl.
CPC ......... *A61L 27/3834* (2013.01); *A61L 27/3604* (2013.01); *A61L 27/3654* (2013.01); *A61L 27/3687* (2013.01); *A61F 2/08* (2013.01); *A61L 2430/06* (2013.01)
USPC ............................ 424/93.7; 424/423; 424/488

(58) Field of Classification Search
None
See application file for complete search history.

(56) References Cited

U.S. PATENT DOCUMENTS

| | | | |
|---|---|---|---|
| 6,376,244 B1 | 4/2002 | Atala | |
| 6,576,265 B1 | 6/2003 | Spievack | |
| 6,689,161 B2 | 2/2004 | Chen et al. | |
| 6,753,181 B2 | 6/2004 | Atala | |
| 6,866,686 B2 | 3/2005 | Ollerenshaw et al. | |
| 6,893,653 B2 | 5/2005 | Abraham et al. | |
| 6,893,666 B2 | 5/2005 | Spievack | |
| 6,933,103 B1 | 8/2005 | Klein et al. | |
| 6,962,814 B2 | 11/2005 | Mitchell et al. | |
| 6,998,418 B1 | 2/2006 | Sung et al. | |
| 7,087,089 B2 | 8/2006 | Patel et al. | |
| 7,108,721 B2 | 9/2006 | Huckle et al. | |
| 7,201,917 B2 | 4/2007 | Malaviya et al. | |
| 7,326,571 B2 | 2/2008 | Freyman | |
| 7,498,412 B2 | 3/2009 | Huang et al. | |
| 7,829,108 B2 | 11/2010 | Van Dyke et al. | |
| 8,221,777 B2 | 7/2012 | Van Dyke et al. | |
| 2002/0119437 A1 | 8/2002 | Grooms et al. | |
| 2003/0014126 A1 | 1/2003 | Patel et al. | |
| 2003/0026787 A1 | 2/2003 | Fearnot et al. | |
| 2005/0013870 A1 | 1/2005 | Freyman et al. | |
| 2005/0234549 A1 | 10/2005 | Kladakis et al. | |
| 2006/0275377 A1 | 12/2006 | Gomes et al. | |
| 2007/0248638 A1* | 10/2007 | Van Dyke et al. | 424/422 |
| 2010/0152852 A1* | 6/2010 | Ingham et al. | 623/14.12 |
| 2012/0259415 A1 | 10/2012 | Van Dyke et al. | |

OTHER PUBLICATIONS

Yamasaki et al, J Biomed Mater Res, 2005, vol. 75A, pp. 23-30.*
Adesida et al, Arthritis Res & Ther, 2006, vol. 8, No. 3, (9 pages).*
Quinn et al, J Cell Sci, 1998, vol. 111, No. 5, pp. 573-583.*
Badylak SF. The extracellular matrix as a scaffold for tissue reconstruction. Semin. Cell Dev. Biol. 13(5):377-383 (2002).
Poehling GG et al. Analysis of outcomes of anterior cruciate ligament repair with 5-year follow-up: allograft versus autograft. Arthroscopy. 21(7):774-785 (2005).
Whitlock PW et al. A naturally derived, cytocompatible, and architecturally optimized scaffold for tendon and ligament regeneration. Biomaterials. 2007; 28; 4321-4329.
International Search Report and Written Opinion, PCT/US07/09781, mailed Oct. 2, 2008.
Supplementary European Search Report, EP 07755875, mailed Nov. 11, 2010.
International Search Report and Written Opinion, PCT/US2010/028313, mailed May 18, 2010.
Lee GM and Loeser RF. Interactions of the chondrocyte with its pericellular matrix. Cells and Materials. 1998; 8: 135-149.

* cited by examiner

*Primary Examiner* — Allison Fox
(74) *Attorney, Agent, or Firm* — Myers Bigel Sibley & Sajovec, P.A.

(57) ABSTRACT

Provided herein are methods of producing a meniscus scaffold to remove material and increase the pore size and porosity therein. In some embodiments, methods include seeding the tissue with allogeneic or autogeneic cells. Bioscaffolds produced by the processes described herein are also provided, as are methods of treating a subject in need of a bioscaffold implant.

15 Claims, 8 Drawing Sheets

Scaffolds after 12 hours

Dynamic Seeding        Static Seeding

5%

7.5%

10%

TISSUE ENGINEERED MENISCUS SCAFFOLDS AND METHODS OF USE

RELATED APPLICATIONS

This application is a 35 U.S.C. §371 national phase entry of PCT Application PCT/US2010/028313, filed Mar. 23, 2010, and published in English on Sep. 30, 2010, as International Publication No. WO 2010/111263, and claims the benefit under 35 U.S.C. §119(e) of U.S. Provisional Patent Application Ser. No. 61/162,433, filed Mar. 23, 2009, the disclosure of each of which is incorporated herein by reference in its entirety.

FIELD OF THE INVENTION

The present invention concerns tissue engineering scaffolds and methods of making and using the same.

BACKGROUND OF THE INVENTION

Meniscectomy is the most common orthopaedic surgical procedure performed in the United States. The meniscus plays a critical role in knee joint biomechanics. Loss of meniscus function can lead to articular cartilage degeneration and osteoarthritis. Current treatment options for meniscus injury are meniscus repair when possible, partial meniscectomy, total meniscectomy, or fresh frozen meniscus allograft transplantation.

There remains a need for an improved bioscaffold that may be used for meniscus implantation that provides an ideal substrate on which cells can grow.

SUMMARY OF THE INVENTION

Provided are methods of producing a meniscus scaffold, including decellularizing a meniscus tissue (e.g., human meniscus tissue) with an oxidant and detergent (e.g., simultaneously) to remove extraneous material and increase the pore size and porosity therein. In some embodiments, methods include applying stress such as mechanical stress (e.g., compression from 0, 0.001, 0.1 or 1 to 10 or 20%) to the tissue in a bioreactor system.

In some embodiments, methods include seeding the tissue with allogeneic or autogeneic cells (e.g., mesenchymal stem cells), and may be either before or after applying a mechanical stress.

In some embodiments, methods include growing the cells in an oxygen tension (e.g., from 0, 0.5, 1 or 2 to 8, 10 or 15% $O_2$).

In some embodiments, methods include exposure to one or more growth factors (e.g., FGF-2, GDF-5 and/or TGF-$\beta$1).

Bioscaffolds (seeded and unseeded) produced by the processes described herein are also provided.

Methods of treating a subject in need of a bioscaffold implant are provided (e.g., for treatment for or prevention of osteoarthritis), including implanting the bioscaffold subject in a treatment effective configuration (e.g., into a knee joint). In some embodiments, cells are seeded intra-operatively or pre-operatively. In some embodiments, cells are selected from a fraction of the subject's blood, bone marrow or fraction of bone marrow, or adipose tissue fraction.

A further aspect of the present invention is a method of seeding a bioscaffold with mammalian cells (e.g., human, dog, cat, pig, cow, rat, mouse cells, etc.) said seeding carried out either in vitro or in vivo, wherein a bioscaffold produced as described herein is utilized for said seeding.

Another aspect of the present invention is the use of a bioscaffold as described herein for the preparation of a graft or transplant for carrying out a method of treatment (e.g., for osteoarthritis) as described herein.

The present invention is explained in greater detail in the drawings herein and the specification set forth below.

DETAILED DESCRIPTION OF THE PREFERRED EMBODIMENTS

Figure 1:
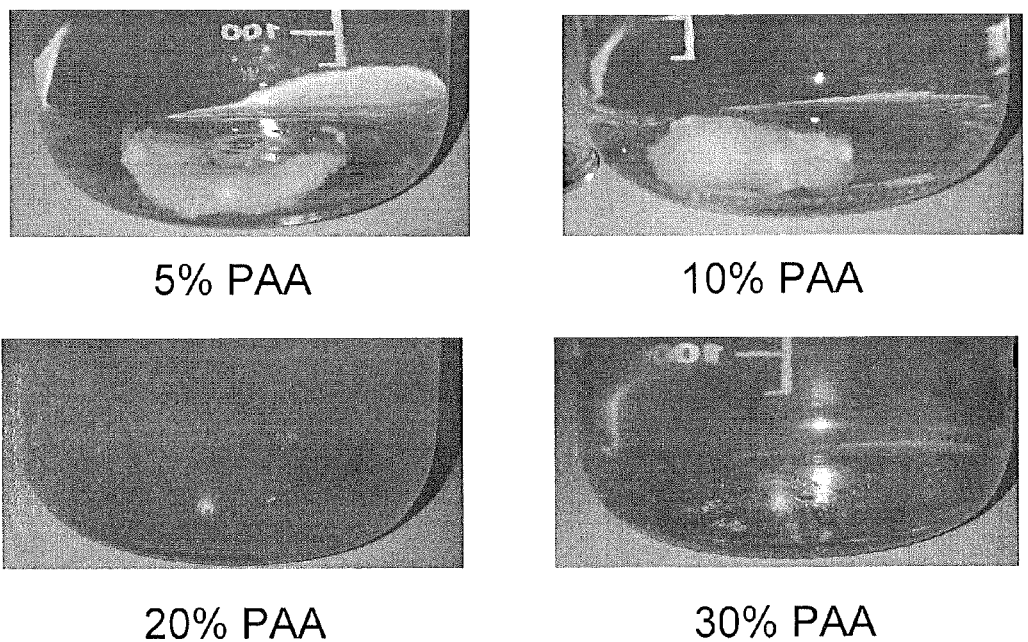
FIG. 1. Scaffolds were oxidized using peracetic acid.

Disclosed herein are bioscaffolds derived from meniscus tissue via mechanical processes and/or chemical treatments. An architecturally optimized scaffold according to some embodiments may be able to withstand early motion and rehabilitation better than previous scaffolds, which would allow earlier functional recovery and accelerate healing after implantation. In addition, improved cell seeding and infiltration of autologous cells is achieved in some embodiments.

In preferred embodiments, improved bioscaffolds disclosed herein are: 1) derived from natural tissue and amenable to host-cell mediated remodeling in vivo, 2) decellularized to minimize inflammatory potential and host immune response, 3) biocompatible, 4) modified to allow seeding, infiltration, and attachment of the patient's own cells prior to or after implantation, and 5) have optimum biomechanical integrity to withstand rehabilitation upon tissue remodeling within the recipient.

As used herein in the description of the invention and the appended claims, the singular forms "a," "an" and "the" are intended to include the plural forms as well, unless the context clearly indicates otherwise. Furthermore, the terms "about" and "approximately" as used herein when referring to a measurable value such as an amount of a compound, dose, time, temperature, and the like, is meant to encompass variations of 20%, 10%, 5%, 1%, 0.5%, or even 0.1% of the specified amount. Also, as used herein, "and/or" refers to and encompasses any and all possible combinations of one or more of the associated listed items, as well as the lack of combinations when interpreted in the alternative ("or").

The disclosures of all United States patent references cited herein are hereby incorporated by reference herein in their entirety.

"Bioscaffolds" or "scaffolds" as used herein refer to a substrate on which cells can grow. In preferred embodiments, the bioscaffolds are derived from natural tissues. These scaffolds are useful in both the medical and research settings.

"Natural tissues" are tissues that are normally found in an animal without human manipulation. Tissues that may be used to carry out the present invention may be from any suitable animal source, including human, other mammalian (e.g., cat, dog, pig, cow, sheep, horse, monkey), avian (e.g., chicken, turkey, duck, goose, etc.), reptile, amphibian, etc. Tissues may be of any suitable type, including but not limited to: blood vessel (e.g., vein, artery) tendon, ligament, fascia, skeletal muscle, smooth muscle (e.g., bladder), cardiac muscle or heart, small intestine, large intestine, kidney, liver, pancreas, nerve (including peripheral nerve), skin, cartilage, meniscus, intervertebral discs, and bone.

More dense tissues (e.g., tissues that bear/transmit/absorb mechanical load as their primary function such as tendon, ligament, bone, meniscus, and intervertebral discs), such as the human Achilles tendon, which is commonly used for ligament reconstruction, may not decellularize to the same extent as less dense tissues. However, techniques taught herein have proven successful in such dense tissues. See U.S. Patent Publication No. 2007/0248638 to Van Dyke et al., which is incorporated by reference herein.

"Subjects" as used herein are preferably human, but also includes other mammals (e.g., cat, dog, pig, cow, sheep, horse, monkey), birds (e.g., chicken, turkey, duck, goose, etc.), reptiles, amphibians, etc.

"Grafting" as used herein refers to the placement of a biocompatible substrate, such as a bioscaffold, into a subject, with or without prior seeding and/or infiltration of cells. Similarly, "transplanting" refers to the taking of a whole or partial organ from one subject and placing it into another, or from one site to another site of the same subject. Cells can be autogeneic (i.e., from the subject to be treated, also known as "autologous"), isogeneic (i.e., a genetically identical but different subject, e.g., from an identical twin), allogeneic (i.e., from a non-genetically identical member of the same species, used in "allograft") and/or xenogeneic (i.e., from a member of a different species, used in "xenograft"). Cells may be obtained from a donor (either living or cadaveric) or derived from an established cell line. To obtain cells from a donor (e.g., a potential recipient of a bioscaffold graft), standard biopsy techniques known in the art may be employed. Representative techniques are described, for example, in U.S. Pat. No. 6,536,567.

Bioscaffolds of some embodiments can be grafted with or without prior seeding with cells. The bioscaffolds of some embodiments an also be used for tissue regrafting as described in U.S. Pat. No. 7,108,721 to Huckle et al. The bioscaffolds of some embodiments may also be used in a bioreactor system, such as that described in U.S. Pat. No. 6,562,616 to Toner et al.; U.S. Pat. No. 5,459,069 to Palsson et al.; and U.S. Pat. No. 4,937,196 to Wrasidlo et al.

In some embodiments, grafting or transplanting may be carried out in order to repair, reconstruct, regenerate, replace, etc., various tissues, especially in applications where sufficient allograft or autograft tissue may not be available, such as tumor, trauma, infection, congenital/developmental deficiencies, and diseases such as arthritis. For example, the bioscaffold may be used in subjects with mild to early moderate osteoarthritis with meniscus degeneration (identified, e.g., with MRI) and early joint narrowing.

"Osteoarthritis" ("OA") or "degenerative arthritis" is a disease in which the articular cartilage, and in some instances the subchondral bone tissue, of a joint deteriorates. Symptoms of osteoarthritis include joint pain, tenderness, stiffness, crepitus, locking of joints and/or inflammation. Osteoarthritis may be "primary," a degenerative disorder related to (but not necessarily caused by) aging of the joints, or caused by and/or associated with ("secondary" to) other factors, injuries or diseases such as congenital joint disorders, diabetes, inflammatory diseases, joint injury, joint infection (septic arthritis), obesity, etc.

Diagnosis, assessment and/or monitoring of OA may be performed radiographically with x-rays, MRI, and/or with clinical function scores, as known in the art, to determine, e.g., loss of joint cartilage, narrowing of the joint space between adjacent bones, bone spur formation, etc. The severity of osteoarthritis may be determined by established scoring systems of semi-quantitative radiography. Mild to early moderate osteoarthritis may be determined, for example, by a grade 0-1 Osteoarthritis Reseach Society International (OARSI) radiograph and/or a grade 0-2 Kellgren-Lawrence plain radiograph, and/or with absence of diffuse chondral deficiency findings on MRI, as known in the art. See Guermazi et al., Plain Radiography and Magnetic Resonance Imaging Diagnostics in Osteoarthritis: Validated Staging and Scoring, J Bone Joint Surg Am. 2009; 91:54-62, for a review on currently applied radiographic and megnetic resonance imaging staging and scoring methods for the assessment of osteoarthritis of the knee.

Chemical Treatments

Chemical treatments for modifying natural tissues to form bioscaffolds are useful in the present invention. The chemical treatments can be closely controlled or titrated so as to increase the pore size in the scaffolds and remove extraneous ECM materials, creating adequate space for infiltrating cells while maintaining a native matrix for attachment. In preferred embodiments, the chemical treatments are performed with oxidants, which etch extraneous ECM.

The "extracellular matrix" or "ECM" as used herein is any part of a tissue that is not a part of any cell. The ECM is the defining feature of connective tissue. In animals, the ECM is comprised primarily of collagen. The ECM also contains various proteins, including a wide range of cellular growth factors.

The increase in pore size and porosity achieved through chemical treatment according to some embodiments improves initial cell seeding and reduces remodeling time. Removal of DNA and other cell matter from the bioscaffold serves to reduce immunogenic foreign body reaction of the recipient subject. Though not all of the DNA must be removed, the more severe the foreign body reaction, the more likely the bioscaffold is to fibrose. Therefore, in preferred embodiments, DNA is removed such that only a mild or moderate transient foreign body reaction is instigated by grafting or transplanting the prepared bioscaffolds. By increasing pore size and porosity and decreasing cellular content in the bioscaffold, cellular in-growth can be enhanced and immunologic response can be reduced. For example, DNA content may be decreased by 30, 40, 50, 60, 70, 80 or 90 percent or more as compared to the harvested natural tissue scaffold prior to processing.

"Oxidants" that may be used to carry out the present invention are found, for example, in U.S. Pat. Nos. 7,029,508; 7,008,593; and 7,008,545. Oxidants may be per compounds or peroxy compounds such as a percarboxylic acid (performic acid, peracetic acid, perpropionic acid, perbenzoic acid, etc.), persulfate, perphosphate, periodate, etc.; peroxy compounds such as alkali and alkaline earth perborate salts, alkali and alkaline earth percarbonate salts, alkali and alkaline earth persulfate salts, hydrogen peroxide, percarboxylic acid and peracetic acid, hypochlorous acid or alkali and alkaline earth hypochlorite salts; etc.; hydroxylamines, ozone, etc., and combinations of the foregoing. The oxidant may comprise one or more of the foregoing in an aqueous solution in, for example, an amount from about 0.01% to about 50% by weight. In preferred embodiments, the oxidant comprises from about 0.5% to about 10% by weight.

As used herein, "increasing the pore size and porosity" refers to the controlled dissolving of the interstitial structure of the bioscaffold in order to create an average pore size and porosity ideal for efficient cellular infiltration. "Pore size" refers to the two-dimensional measurement of empty or void space present in a tissue, while "porosity" refers to the three-dimensional measurement of empty space or void volume per total volume. As those skilled in the art will appreciate, the ideal pore size and porosity will vary from tissue to tissue. It will also be understood that the treatments disclosed herein that increase the average pore size in the bioscaffolds disclosed herein also have the effect of increasing the porosity of the tissue.

In some embodiments, average pore sizes are large enough to accommodate an intact cell. For example, in some embodiments the resulting pore sizes have an average diameter greater than 1 micron, and more preferably greater than 50 microns. In other embodiments, the pore size may be 100 microns or more in average diameter. In some embodiments, the ideal pore size of scaffolds developed using the processes described herein on bone tissue is from 400-1000 microns. In some embodiments, the ideal pore size of ligament, tendon, and meniscus tissues is from 100-1000 microns. In some embodiments, the average pore size is increased by approximately 3 times the cell diameter of the cell intended to be seeded into the bioscaffold.

In some embodiments, pore sizes of the scaffold have an average cross sectional area of from 10 $\mu m^2$ to 1000 $\mu m^2$, or 25 $\mu m^2$ to 800 $\mu m^2$, or 50 $\mu m^2$ to 650 $\mu m^2$, or 70 $\mu m^2$ to 500 $\mu m^2$, or 90 $\mu m^2$ to 400 $\mu m^2$. For example, in some embodiments a harvested meniscus scaffold after processing may have pore sizes with an average cross sectional area of between 80 and 600 $\mu m^2$, with the pore size of the inner region increasing from 50-60 $\mu m^2$ to 85-100 $\mu m^2$ and the pore size of the outer region increasing from 70-80 $\mu m^2$ to 300-500 $\mu m^2$ in some embodiments. The pore size can be measured by techniques known in the art, e.g., scanning electron micrograph analysis.

Cells that can be seeded into the bioscaffold include stem cells (pluripotent and/or multipotent), adipose cells, tendon cells, chondrocyte cells, skeletal muscle cells, osteocyte cells, etc., without limitation (See, e.g., U.S. Pat. No. 6,808,704 to Lanza et al.; U.S. Pat. No. 6,132,463 to Lee et al.; and U.S. Patent Application Publication No. 2005/0124003 to Atala et al.). In some embodiments, the average pore size is approximately three times a cell diameter of 1 to 30, 40, or 50 or more microns (i.e., 3 to 60, 80, or 100 or more microns).

The ideal pore size may also be represented as a percentage of the average pore size of the tissue before the controlled dissolving of the interstitial structure. In some embodiments, the average pore size is increased by 20, 30, 40, or 50%. In other embodiments, the average pore size is increased by 60, 70, 80, 90, or 100% or more. In other embodiments, the average pore size is increased by 150, 200, 250, 300, or 350% or more. However, the overall structural integrity necessary for the intended application must be considered when selecting for the ideal resultant pore size.

In some embodiments, cells include blood cells, bone marrow cells, and/or adipose-derived cells. In some embodiments, cells are mesenchymal stem cells.

In some embodiments, cells are seeded intraoperatively. In other embodiments, cells are seeded onto the bioscaffold pre-operatively with adequate time allowed from cell attachment and infiltration into the bioscaffold, and in some embodiments the seeded bioscaffold is pre-conditioned in a suitable bioreactor system under physiological stresses, e.g., oxygen tension, hydrostatic pressure and/or mechanical forces and/or growth factor supplementation. In other embodiments, the bioscaffold is pre-conditioned in a suitable bioreactor system prior to seeding, such that the cells (seeded, exogenous cells and/or native, endogenous cells of the subject into which the bioscaffold is implanted) can rebuild the remaining pericellular matrix, guided along the differentiation path by the still remaining exprecellular matrix of collagens, proteoglycans, integrins, etc., while still permitting host vascularization and surrounding tissue integration upon implantation.

In some embodiments, production of bioscaffolds is conducted by first decellularizing the tissue of interest, for example, by the following procedures:

1. Pre-treat the tissue with deionized (DI) water or other hypotonic solution to disrupt the cells (e.g., for 12, 24, 36, 48 or 60 hours, optionally on a shaker, and optionally replacing the water every 12 or 24 hours);
2. Optionally, treat the disrupted tissue with an enzyme such as trypsin to break down cell adhesions (e.g., for 12, 24, 36 or 48 hours);
3. Optionally, treat the tissue with media such as DMEM High Glucose supplemented with 1% antibiotic/antimitotic (supplemented with serum in some embodiments, e.g., 10% FBS) (e.g., for 12, 24, 36 or 48 hours) to help neutralize the enzyme.
4. Treat the tissue with detergent solution such as 0.5-4% Triton X-100 (a nonionic surfactant) in 1-5% peracetic acid in deionized water (e.g., for 12, 24, 36 or 48 hours) to remove cell debris and/or increase the pore size and porosity of the scaffold.
5. Optionally, but preferably, wash residual reagents out of the bioscaffold with repeated washes of DI water. Presence of peracetic acid, for example, may be detected by pH measurement (e.g., with a test strip).

These steps, or any one of them, may optionally be performed at 37 degrees Celsius in some embodiments. Any step may be repeated 2 or more times, if desired.

In some embodiments, the decellularizing step may be carried out as described in U.S. Pat. No. 6,753,181 to Atala, by: mechanically agitating tissue (e.g., a complete organ or a portion thereof) in membrane stripping fluid to disrupt cell membranes while maintaining the interstitial structure of the tissue; treating the isolated tissue in a solubilizing fluid at a concentration effective to extract cellular material from the tissue while maintaining the interstitial structure of the tissue; and optionally washing the isolated tissue in a washing fluid to remove cellular debris while maintaining the interstitial structure of the tissue until the isolated tissue is substantially free of cellular material, to thereby produce a decellularized tissue scaffold (in some embodiments washing may optionally be deferred until after the oxidizing step).

The step of mechanically agitating the tissue may comprise placing the tissue in a stirring vessel having a paddle that rotates at a speed ranging from about 50 revolutions per minute (rpm) to about 150 rpm. The step of mechanically agitating the isolated tissue may occur in a non-detergent membrane stripping fluid (e.g., distilled water, physiological buffer or culture medium). The step of treating the isolated tissue in the solubilizing fluid may also occur in a stirring vessel. The treating step may comprise using a solubilizing fluid that is an alkaline solution having a detergent. The treating step may comprise treating the isolated tissue in an alkaline solution (for example, a solution selected from the group consisting of sulphates, acetates, carbonates, bicarbonates and hydroxides, and a detergent selected from the group consisting of Triton X-100, Triton N-101, Triton X-114, Triton X-405, Triton X-705, and Triton DF-16, monolaurate (Tween 20), monopalmitate (Tween 40), monooleate (Tween 80), polyoxyethylene-23-lauryl ether (Brij 35), polyoxyethylene ether W-1 (Polyox), sodium cholate, deoxycholates, CHAPS, saponin, n-Decyl β-D-glucopuranoside, n-heptyl β-D glucopyranoside, n-Octyl α.-D-glucopyranoside and Nonidet P-40).

The examples of decellularization techniques provided above are not intended to be limiting, and the invention encompasses the use of essentially any decellularization technique that removes a substantial fraction of the cells while leaving the interstitial structure substantially intact. Alternatively, the decellularization may be combined with the chemical modifications as described below to remove extraneous ECM materials and increase the average pore size.

It will be appreciated by those skilled in the art that certain techniques will be preferred for particular tissue engineered constructs or native tissues, depending upon the properties of these constructs or tissues. An appropriate decellularization technique may be selected and parameters such as temperature and time may be optimized in order to achieve a desired degree of decellularization. In some embodiments of the invention the decellularization process removes at least 50% of the cells. In some embodiments of the invention the decellularization process removes at least 60%, at least 70%, or at least 80% of the cells. In some embodiments of the invention at least 90%, at least 95%, or substantially all of the cells are removed. As described above, there may be a tradeoff between the two goals of achieving a high degree of decellularization and preserving the structure and properties of the extracellular matrix. Thus it is not necessarily preferred to achieve maximal possible decellularization if doing so results in unacceptable damage to the extracellular matrix. The optimum degree of decellularization may depend upon the properties of the construct and the use for which it is intended.

In some embodiments, the bioscaffold is also treated with an oxidant solution to effectively remove extraneous ECM materials and increase the average pore size. Any type of water-soluble oxidant can be used. Preferred oxidants include hydrogen peroxide and peracetic acid. The decellularization and oxidizing steps may also be combined, or the oxidizing step may be performed before the decellularization step.

Typical oxidant concentrations range from 0.5, 1, 1.5, 2, 2.5, 3, 3.5, 4, 4.5, 5, 5.5, 6, 7, 8, 9, or 10%, and up to 20% (w/v) and will vary depending on the starting density of the tissue and desired degree of porosity. A preferred concentration for meniscus tissue is between 0.5 and 10% (e.g., 2.5%). After oxidation, residual chemicals may be removed by repeated washes with DI water and conditioned in a final step by incubation with phosphate buffered saline (PBS). The scaffold may also be freeze-dried and sterilized (e.g., by cold gas) prior to use.

For chemical modification, a batch process can be used to modify large numbers of bioscaffolds at one time. The increase in porosity can be controlled as in any kinetic process by changing oxidant concentration, time, and temperature. Similar to the decellularization step discussed above, there may be a tradeoff between the two goals of achieving adequate porosity and preserving the structure and properties of the extracellular matrix. Thus, it is not necessarily preferred to achieve maximal possible porosity if doing so results in unacceptable damage to the extracellular matrix. The optimum degree of porosity may depend upon the properties of the construct and the use for which it is intended.

In preferred embodiments, the oxidant is added sequentially or simultaneously with a detergent. Simultaneously is close enough in time that combining the two steps (oxidant and detergent) will increase removal of cellular material and DNA. In some embodiments, using oxidant and detergent simultaneously increases the removal of DNA and minimizes residual DNA, in turn minimizing immunogenic and inflammatory potential of the implanted scaffold in the host after implantation and promoting host cell infiltration into the scaffold in vivo or in vitro.

These disclosed modifications will decrease the time necessary for cellular repopulation in vivo or cell seeding in vitro and reduce the time necessary for remodeling of collagen fibrils, which subsequently improves the biomechanical integration of the scaffolds in vivo. All of these factors have been implicated in the poor incorporation of current grafts used by others in reconstruction of tissues. The removal of extraneous cellular material greatly reduces the potential for inflammation and disease transmission upon implantation of the scaffold.

Cultivation of Scaffolds by Applied Stresses/Chemical Factors

In some embodiments, seeded scaffolds are grown under stress conditions such as mechanical forces, fluid flow and/or reduced oxygen tension, e.g., by a suitable bioreactor system.

In some embodiments, environmental stress is induced by fluid flow and/or mechanical stimuli such as dynamic, static or shear forces to modulate cell expression and differentiation. In some embodiments, stress is applied in physiological frequencies, which may be similar to that which occurs to the tissue in vivo. A bioreactor system may be used to condition the seeded bioscaffold. In some embodiments, mechanical load of compression of 0, 0.001, 0.1 or 1 to 10 or 20% is applied.

In some embodiments, oxygen tension is controlled, e.g., to induce hypoxic condition and promote the survival of cells adapted to a hypoxic condition, e.g., in a suitable bioreactor system. In some embodiments, the oxygen tension is from 0, 0.5, 1 or 2 to 8, 10 or 15% $O_2$.

In some embodiments, soluble growth/differentiation factors are added to influence/promote functional tissue development of the meniscus scaffold. Proteins (such as growth factors) or other additives (such as antibiotics, anti-inflammatories, and modulators of the immune response) may also be added to the cell and/or bioscaffold preparations at any time. Also, various treatments may be applied to enhance adherence of cells to the substrate and/or to each other. Appropriate treatments are described, for example, in U.S. Pat. No. 5,613,982. Such treatments include the application of various proteins, e.g., growth factors or extracellular matrix proteins to the bioscaffold substrate or to the growing construct. For example, collagen, elastin, fibronectin, laminin, or proteoglycans may be applied to the bioscaffold. The bioscaffold can be impregnated with growth factors such as nerve growth factor (NGF), aFGF, bFGF, PDGF, TGFβ, VEGF, GDF-5/6/7, BMP-1/2/3/4/5/6/7/13/12/14, IGF-1, etc., or these agents may be provided in the culture medium.

In some embodiments of the invention, the cells employed have been genetically manipulated by the introduction of exogenous genetic sequences or the inactivation or modification of endogenous sequences. For example, genes may be introduced to cause the cells to make proteins that are otherwise lacking in the host. Production of scarce but desirable proteins (in the context of certain tissues) may be enhanced, e.g., growth or differentiation factors.

The present invention is explained in greater detail in the following non-limiting Examples.

EXAMPLES

Example 1

Meniscus Scaffolds

Medial menisci from sheep were harvested. The menisci were decellularized and treated with oxidant to increase pore size and porosity using aqueous Triton X-100 and peracetic acid. Tissue was equilibrated in phosphate buffered saline (PBS). The contralateral medial meniscus was used as a control. The central ⅓ body of each meniscus was fixed in 10% formalin and paraffin processed. Sections were cut in the coronal plane and stained with hematoxylin and eosin (H&E) for routine cellular assessment and 4',6-diamidino-2-phenylindole (DAPI) to identify residual nuclear components. Samples were assessed using light microscopy. DNA was then isolated using a commercially available kit (DNEasy, Qiagen, Valencia, Calif.). The DNA concentration in the resulting volume was used to calculate total DNA content, which is standardized using the initial dry weight of the sample. These values were averaged, a standard deviation was determined, and a comparison made using a Student's unpaired t-test with a p-value <0.05 accepted for statistical significance. The architecture of the sheep intact meniscus and the meniscus scaffold was examined using scanning electron microscopy (SEM). Specimens were examined in the coronal plane. Porosity was qualitatively compared between the intact meniscus and meniscus scaffold.

Upon gross inspection, the decellularization and oxidative treatment did not change the general shape and architecture of the meniscus. The histological findings clearly indicate a decrease in cellular and nuclear content. The H&E stained sections also show an increase in porosity. DAPI nuclear staining revealed a decrease in nuclear content in the scaffold compared to the intact fresh frozen meniscus. DNA content analysis showed a decrease in DNA content in the scaffold compared to the intact meniscus.

SEM images confirmed an increase in pore size and porosity in the scaffold compared to the intact meniscus. The SEM also showed that the architecture of the meniscus is intact. These results indicate that the decellularization and chemical oxidation treatments decrease DNA content in a meniscus scaffold, and that the extracellular matrix architecture of the meniscus remains intact. This process is able to increase pore size and porosity and decrease nuclear content, providing an improved scaffold that minimizes immunologic response and encourages cellular in-growth.

Example 2

Initial studies were performed using rabbit tissue and demonstrated successful decellularization of meniscus tissues with approximate 80% reduction of DNA content and absence of fluorescent nuclear staining on histology exam. Tissue integrity and structure was maintained.

We transitioned to the study of sheep tissue to facilitate mechanical testing of scaffolds and also allow for in vivo testing using a large animal meniscus transplant surgical model. Preliminary histology and fluorescent staining of sheep tissue demonstrated successful decellularization of tissue with absence of fluorescent nuclear staining. Additional oxidative reactions with assessment of pore size by SEM imaging and micro CT has been performed. DNA content reduction of 60% was achieved.

Initial scaffold seeding studies to determine optimum pore size for cell growth have been performed. NIH-3T3 fibroblasts have been seeded on scaffold plugs obtained from decellularized/oxidized ovine meniscus tissue. Static, dynamic, and centrifugation seeding techniques have been performed on scaffolds oxidized using oxidant concentrations ranging from 1.5%-10% peracetic acid/2% Triton X-100 scaffolds/48 hour processing for a duration of up to 4 weeks in culture (FIG. 1). Loss of tissue integrity and gross structure was noted in 10% peracetic acid treated scaffolds.

Figure 2:
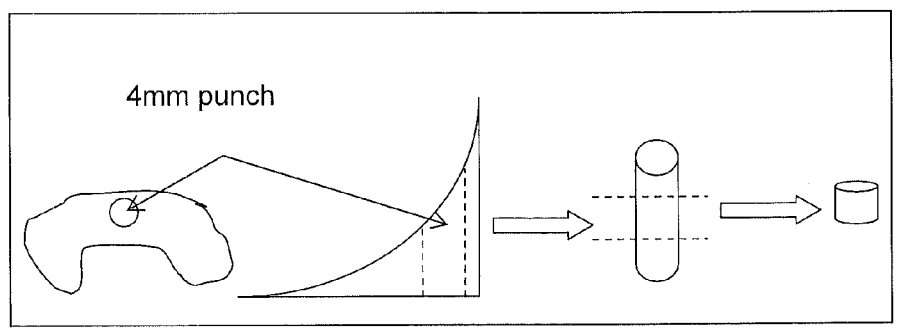
FIG. 2. Scaffold discs were created from 4 mm punches of the tissue and seeded both statically and dynamically.

Scaffold discs were seeded both statically and dynamically (FIG. 2). For dynamic seeding, 100 million NIH 3T3 cells were placed in 100 mL of media in a sterile jar with a stir bar. The scaffolds were placed in the cell suspension and seeded on a stir plate at 80 rpm for 24 hours. The discs were then moved to a 48 well plate for 48 hours followed by a 12 well plate for the duration of the experiment. For static cultures, 1 million cells in 1 mL of media were dripped onto the discs in a 48 well plate. After 72 hours the discs were transferred to a 12 well plate. Both static and dynamic discs were cultured for a total of 14 days.

Figure 3:
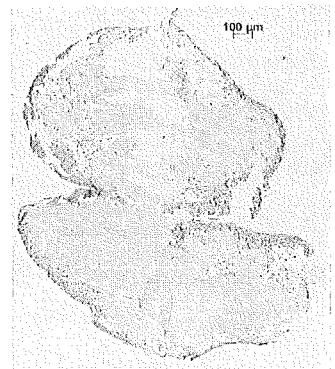
FIG. 3. Both static and dynamic cultures on 5%, 7.5% and 10% peracetic acid allograft scaffolds showed a cell monolayer on the outside of the scaffold with visible cell migration into the scaffold.
Figure 3:
Figure 3:
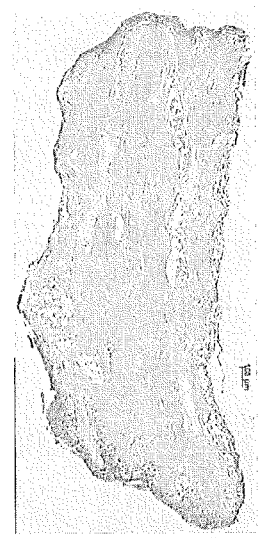
Figure 3:
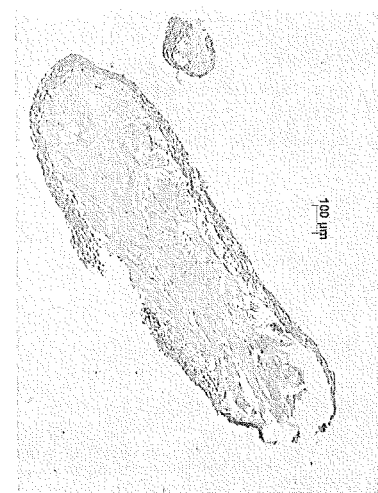
Figure 3:
Figure 3:
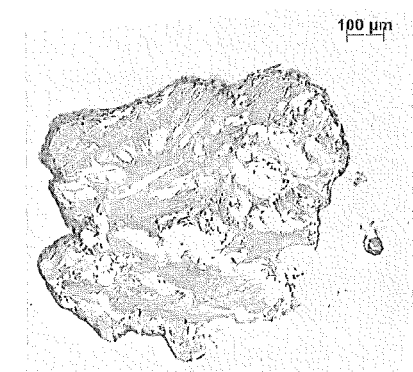

Both static and dynamic cultures showed a cell monolayer on the outside of the scaffold with notation of visible cell migration into the scaffold (FIG. 3). No difference was observed in cell migration or monolayer formation between the static and dynamic cultures. Additional experiments culturing discs for 4 weeks showed improved cellular migration into the central substance of the scaffold. Because there was no significant difference between static and dynamic discs, only static seeding was used in subsequent studies.

Next, seeding studies were performed with bone marrow derived ovine stem cells. Bone marrow biopsies were performed on the iliac crest of mature ovine sheep. A small incision was made above the iliac crest, bone marrow was aspirated out and immediately placed on ice for preservation. Bone marrow aspirate was processed using a histopaque solution to isolate cells. Mesenchymal stein cells (MSCs) were isolated from the mononuclear layer of the histopaque gradient. MSCs were grown on tissue culture plates using DMEM high glucose with 10% FBS and 1% penicillin/streptomycin. Verification of the cell phenotype was achieved using flow cytometry. Positive antibodies used were CD 44, CD105, and vimentin and negative antibodies were CD34 and CD45.

Biopsies of 8 mm were taken from scaffolds prepared with 1.5% and 2.5% peracetic acid/2% Triton X-100 solutions and cut into 2 mm thick discs as described above. Collagen discs (Kensey Nash Biomaterials) and PLLA Biofelt® (Concordia) of the same dimensions as the natural scaffolds were also used for comparison. All scaffolds were seeded with 1 million bone marrow mesenchymal stems cells by slowly dripping the cells onto the scaffolds. Scaffolds were incubated with cells for 2 and 4 weeks to allow for cellular attachment and migration into the scaffolds.

Figure 4:
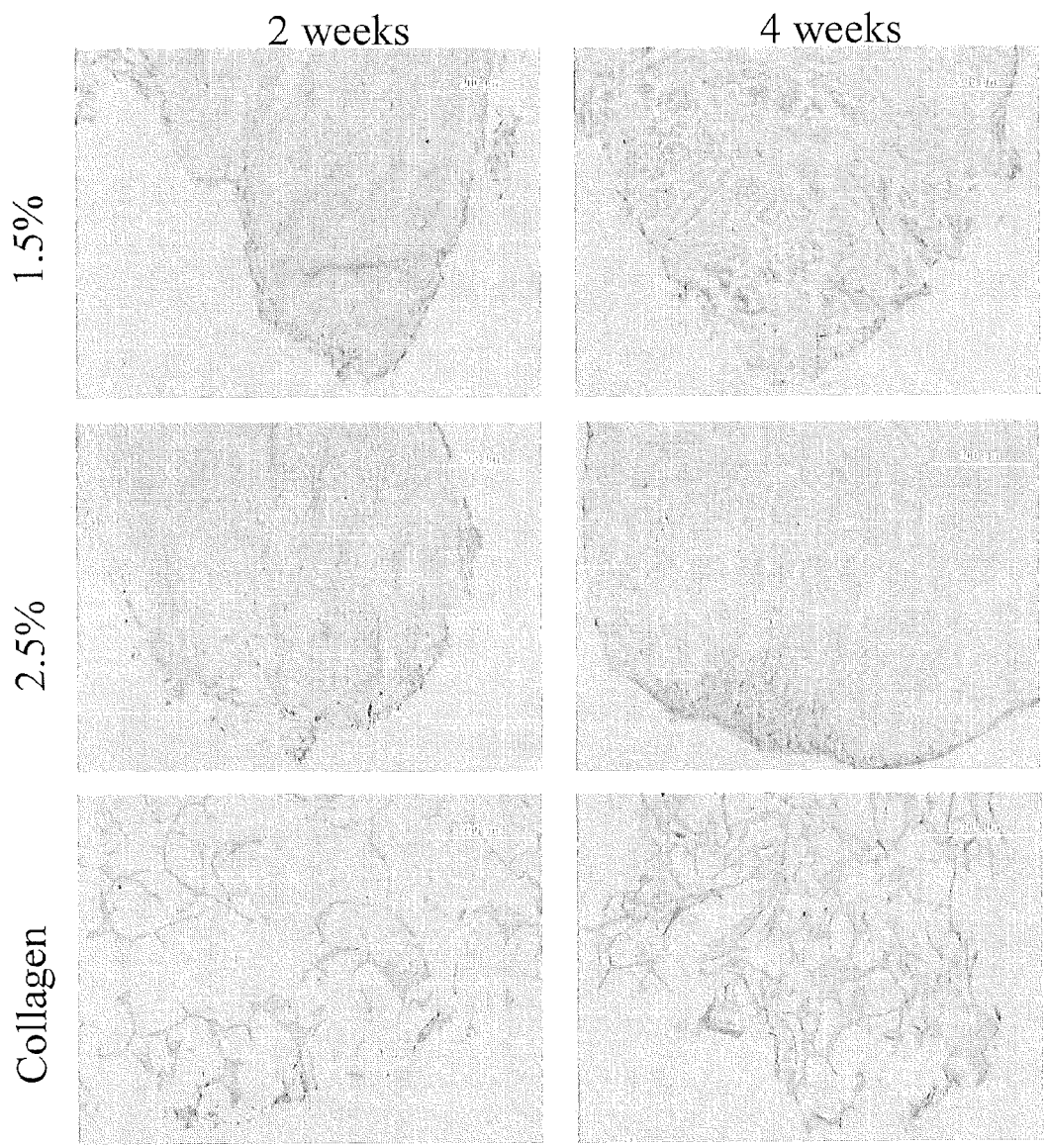
FIG. 4. Cell monolayer was achieved on the outside of both the 1.5% and 2.5% peracetic acid allograft scaffolds at both 2 and 4 weeks. Cell proliferation migration was also observed up to 500 μm into both the 2 week and 4 week meniscus allograft scaffolds. Some cell proliferation and migration was present in the collagen type I scaffolds, however, the collagen type I scaffolds lacked enough structure to allow for the formation of a monolayer.

Cell monolayer was achieved on the outside of both the 1.5% and 2.5% peracetic acid allograft scaffolds at both 2 and 4 weeks (FIG. 4). Cell migration was also observed up to 500 µm into both scaffolds. Some cell proliferation and migration was present in the collagen scaffolds, however, the collagen scaffolds lacked enough structure to allow for the formation of a monolayer.

Example 3

In vivo sheep meniscus transplantation studies have been performed. Initial pilot studies of medial meniscus scaffolds processed using 5% and 7.5%/2% Triton X-100 transplanted into adult sheep and harvested at 6 weeks demonstrated progression of arthritic change and loss of scaffold integrity. This finding, in combination with scaffold development and characterization studies as well as seeding studies supported the selection of 2.5%/2% Triton X-100 as the scaffold processing concentration for the in vivo testing.

Allograft and scaffold (2.5% peracetic acid/2% Triton X-100) medial meniscus constructs with n=8 allograft and n=5 scaffold were transplanted into skeletally mature sheep and harvested at 6 months post surgical.

Analysis is performed with histology, PCR, arthritis and biointegration grading, and biomechanical testing studies. Initial gross analysis of harvested scaffold tissue demonstrated maintenance in tissue architecture and absence of osteoarthritis development comparable to allograft transplant constructs.

Additional in vivo sheep studies investigate stem cell seeded scaffolds and stem cell seeded+in vitro cultivated (3 weeks) scaffolds.

Example 4

Seeding experiments are performed to investigate the effect of hypoxic conditions (1, 5 and 10% $O_2$) on stem cell seeded scaffolds (mesenchymal stem cells and adipose-derived stem cells). Effects on hypoxia-inducible factor (HIF)-1-alpha are measured.

Application of growth factors (FGF-2, GDF-5, and TGF-β1) is also studied, including determination of stem cell differentiation into fibrochondrocytes.

Example 5

Current meniscus scaffolds that are collagen based, porcine small intestinal submucosal based, and polyurethane based all lack the ultrastructure and collagen fiber alignment of the native meniscus. Therefore, such scaffolds may not have the ability to withstand hoop-stresses and the demanding mechanical environment of the knee. The objective of this study was to develop a meniscus scaffold that has increased porosity while maintaining the intact meniscus extracellular matrix ultrastructure to support biomechanical function. We hypothesized that our tissue processing approach will be able to decellularize and increase porosity of fresh frozen meniscus allograft tissue with a limited loss of mechanical properties.

Sixteen skeletally mature ovine knees were harvested for scaffold characterization experiments (n=8 control, n=8 scaffold) and n=16 knees were harvested for biomechanical testing experiments (n=8 control, n=8 scaffold), all female with an age range of 3-4 years old. The medial meniscus of each knee was dissected with root insertions intact, placed in saline soaked gauze and stored in Dulbecco's phosphate buffered saline (Dulbecco's PBS, 1× Dulbecco's phosphate buffered saline, Gibco Invitrogen, Carlsbad, Calif.) at −20° C. until further use. Dulbecco's phosphate buffered saline (Dulbecco's PBS) was used throughout the study.

The goal of this process was to decellularize the entirety of the meniscus to produce an acellular scaffold, and to increase pore size and interconnectivity using a concomitant decellularization and oxidation process. Menisci intended for scaffolds (n=8) were defrosted at room temperature. This tissue underwent a multi-step decellularization process adapted from a previously published technique applied to tendon tissue. Each dissected meniscus was placed in distilled DNAse/RNAse free water (Nanopure Type I Ultrapure Water System, Thermo Fisher Scientific Inc., Waltham, Mass.) and placed onto a rotating shaker (New Brunswick, Edison, N.J.) at 200 rpm and 37° C. for 48 hours to lyse existing cells. The water was discarded and the menisci were then placed in 500 ml of 0.05% trypsin-EDTA (Gibco Invitrogen, Carlsbad, Calif.) solution and returned to the shaker. After 24 hrs the trypsin solution was discarded and 500 ml of Dulbecco's modified Eagle's medium with high glucose (Gibco Invitrogen, Carlsbad, Calif.) mixed with 10% fetal bovine serum (Valley Labs, Winchester, Va.), 100 IU/ml penicillin, 100 mg/ml streptomycin, and 0.25 mg/ml amphoteracin B (Gibco Invitrogen, Carlsbad, Calif.). The menisci were placed back on the shaker for 24 hrs. This step was performed to help neutralize the trypsin. The menisci were then treated with 500 ml of 2% aqueous Triton X-100 (Sigma-Aldrich Corp., St. Louis, Mo.) and 1.5% peracetic acid (Sigma-Aldrich Corp., St. Louis, Mo.) and placed back on the shaker for 48 hours to remove cellular debris and nuclear components and expand existing porosity. The scaffolds were then subjected to multiple washes in 500 ml distilled DNase/RNase free water where the water was changed after 1 hr and subsequently every 24 hrs for 72 hrs at 200 rpm and 37° C. The scaffolds were then washed in 500 ml Dulbecco's PBS for 24 hrs, 200 rpm and 37° C. and subsequently stored in Dulbecco's PBS at −20° C. for future use.

After the anterior and posterior horns were removed for other experiments, a section of the midbody of the meniscus scaffold and intact meniscus were dissected and placed in 10% neutral buffered formalin (Sigma-Aldrich Corp., St. Louis, Mo.) at room temperature for 4 hours. This tissue was then processed for histology, embedded in paraffin, and sectioned on a microtome (5 µm thick) to obtain coronal sections. Sections were mounted on slides and stained using hematoxylin and eosin (H&E, Sigma-Aldrich Corp., St. Lois, Mo.) for cellular assessment and Masson's Trichrome (Sigma-Aldrich Corp., St. Louis, Mo.) to visualize residual collagen in the scaffold. Additionally, 4,6-diamidino-2-phenylindole (DAPI, Vector, Burlingame, Calif.) staining was used to identify residual nuclear components. Representative micrographs were taken at 100× and 200× magnifications for comparison. Samples of both intact meniscus and meniscus scaffolds were obtained from the anterior horn, freeze-dried, weighed, and placed into clean, sterile 1.5 ml micro-centrifuge tubes. DNA was then isolated using a commercially available kit (DNEasy, Qiagen, Valencia, Calif.). The resulting solution was analyzed for DNA content at λ=280 nm with a spectrophotometer (Thermo Spectronic, Biomate 3, Rochester, N.Y.). The DNA concentration was used to calculate total DNA content per dry weight of sample. These values were averaged, standard deviation was determined, and a comparison was made between intact and scaffold tissue using a Student's t-test for unpaired data with a p-value <0.05 accepted for statistical significance.

Initial analysis of the scaffold's biocompatibility was evaluated using in vitro cell viability and metabolic activity assays. These are in vitro cytotoxicity tests that use a direct contact method. Punch biopsies (3 mm diameter) of meniscus scaffold (n=12 wells) were placed in the center of subconfluent murine NIH 3T3 embryonic fibroblast monolayer cultures in 48-well plates (Becton Dickinson, Frankin Lakes, N.J.), covering one-tenth of the surface area according to established standards. The same procedure was followed using latex biopsies (n=12) which are cytotoxic and serve as a negative control. Cells alone served as a positive control (n=12). The cell-material contact was maintained at 37° C. and 5% CO2 for 4 days. The medium was changed every 48 hours. At the end of the incubation, the material fragments were removed and two separate tests (parallel experiments in 48 well plates) were performed to measure metabolic activity (3-(4,5-dimethylthiazol-2-yl)-5-(3-carboxymethoxyphenyl)-2-(4-sulfophenyl)-2H16 tetrazolium, "MTS" assay, Promega, Madison, Wis.) and cell viability, (Neutral Red Assay) described below. For both MTS and Neutral Red, a visible color change in the solution was observed that correlates with cell metabolic activity and cell viability. This color change is related to the amount of light absorbance measured by the spectrophotometer at a specific wavelength ($\lambda$).

Mitochondrial Metabolic Activity Assay:

The cell layers were rinsed with Dulbecco's PBS. Subsequently, 800 µL of MTS solution was added into each well. After a 3-h incubation at 37° C., the absorbance was measured at $\lambda$=490 nm using a spectrophotometer (Biotek, ELX800, Winoski, Vt.). The absorbance obtained is directly proportional to the metabolic activity of the cell populations and inversely proportional to the toxicity of the material.

Cell Viability Assay:

The cells were rinsed with Dulbecco's PBS. Subsequently, 800 µL of Neutral Red solution (Sigma, 0.005% w/v in culture medium) was added to each well. The Neutral Red solution was removed after a 3 hour incubation at 37° C. Dye extraction was then performed by adding 100 µL of 1% (v/v) acetic acid in 50% (v/v) ethanol solution by agitating the plates for 5 min Absorbance was measured at $\lambda$=540 nm using a spectrophotometer (Biotek, ELX800, Winoski, Vt.). The absorbance obtained is directly proportional to the viability of the cell populations and inversely proportional to the toxicity of the material. The results of the mitochondrial metabolic activity and the cell viability assays were reported as means and standard deviations normalized to media alone. Statistical analysis with ANOVA (experimental, positive control, negative control) was performed for each assay with a p-value <0.05 accepted for statistical significance.

Porosity and Pore Interconnectivity

Scanning Electron Microscopy

The architecture of the intact meniscus and the meniscus scaffold was examined using scanning electron microscopy (SEM). Specimens obtained from the anterior horn of the medial meniscus were fixed in 2.5% glutaraldehyde buffered with Dulbecco's PBS (Tousimis, Rockville, Md.) for 24 hours at 40 C and then critically point dried. The samples were mounted on aluminum supports, sputter coated with gold and examined with SEM (Hitachi S-2600N variable pressure scanning electron microscope, Toykyo, Japan). Scans were performed at 500× and 50 kV in inner (avascular) and outer (vascular) regions of coronally cut intact and scaffold meniscus tissue. Pore sizes (area) were determined via image analysis software with a single user to minimize interobserver variablility (MetaMorph, Sunnyvale, Calif.). The average pore size (area) of each meniscus scaffold was determined and compared to the intact meniscus average pore size using an unpaired Student's t-test with a p-value <0.05 accepted for statistical significance.

Micro CT

A 5-6 mm axial segment was cut from each menisci (intact and scaffold) at the junction of the anterior horn and body and placed in 2.5% glutaraldehyde buffered with Dulbecco's PBS for hours at 4° C. After three 10 minute Dulbecco's PBS washes, all fixed specimens were critical point dried. Each dried specimen then was micro CT scanned (Siemens Micro-CAT, Siemens, N.Y.) at 70 kV and 700 projections for 200 degrees of rotation, with 18 µm resolution. All scans were analyzed using a finite element analysis software package (Mimics, Materialize, Leuven/Belgium) to create three-dimensional reconstructions of 1 $mm^3$ volumes of the outer and inner region of each meniscus. A single user analyzed all the specimens to minimize interobserver variablilty. Scaffold porosity was obtained using binary masks to subtract out the meniscus extracellular matrix at a threshold of −592 Hounsfield Units (HU). A ratio of pore volume to cube volume yields the percent porosity for each specimen. Pore volume connectivity, the percentage of the pore volume that is interconnected, was obtained by an algorithm in the finite element software package. Connected pore volume divided by total pore volume yields pore volume connectivity. The percent porosity and pore connectivity in the meniscus scaffold was compared to the intact meniscus using an unpaired Student's t-test with value <0.05 accepted for statistical significance.

Biomechanical Testing

Specimen Preparation

Sixteen ovine knees (8 donors) were dissected and the medial meniscus was harvested. The menisci (right or left) were randomly assigned to the intact meniscus group (n=8) and the contralateral was assigned to the meniscus scaffold group (n=8) to create paired biomechanical data. Specimens obtained for testing were orientated parallel to the tibial surface. The tibial surface from each meniscus was placed against a cryotome (Leica Cryostat, Wtzlar, Germany) stage and frozen. The apex of the femoral surface of the meniscus was removed to create a wide flat surface. The meniscus was then defrosted and flipped over to place the flattened apex on the freezing stage of the cryotome. Once the tissue was frozen in place, 1 mm slices were taken parallel to the tibial surface. Compression and tensile specimens were taken from the slice closest to the tibial surface. The compression specimens were taken (3 mm circular biopsy punch) from the posterior horn. Compression specimens were harvested to test specimens in the direction of axial knee loading. Specimens for tensile testing were obtained from the body of the medial meniscus. The specimens were placed on a light box and cut parallel to the circumferential fibers using a custom made longitudinal punch (4 mm wide). Therefore, tensile specimens were harvested to test in the direction of the circumferential fibers.

Compression Testing Procedure

Unconfined compression experiments were performed using a uniaxial materials testing machine (Instron model 5540, Norwood, Mass.) with a 100N load sensor (±0.25% accuracy). Specimens were thawed at room temperature prior to testing and kept moist with room temperature Dulbecco's PBS. Each sample was placed between the stainless steel test platens and a nominal load of 0.1N was applied; preliminary tests demonstrated that this was just enough load for the platen to engage the specimen. Prior to testing, each sample was preconditioned to 12% strain for 10 cycles with a compression rate of 32%/sec. A stress-relaxation test was then applied to 12% strain at strain rate of 32%/sec. This strain rate was based on a physiologic single leg stance of 0.38 seconds, which corresponds to 0.32 mm/sec. Samples reached equilibrium in approximately 30 min. Stress equilibrium was defined as less than 1% change in stress per 1 min. Two tests were performed per specimen.

Compression Data Analysis

The compressive modulus was determined from stress strain curves using Fung's two parameter exponential model 59, where σ is the load applied divided by the cross sectional area prior to testing and ε is the strain applied. Equation (1) was fit using the method of least squares (Matlab v.7, Natick, Mass.) to the linear portion of the stress-strain curve to determine parameters A and B. The modulus was calculated from A and B using equation (2).

$$\sigma = A^*(\exp(\epsilon^*B) - 1) \quad (1)$$

$$d\sigma/d\epsilon = B(\sigma + A) \quad (2)$$

Tensile Testing Procedure

Tensile specimens (intact meniscus and meniscus scaffold) were kept moist with Dulbecco's PBS. The ends of each specimen were mounted using pneumatically controlled soft tissue 268 clamps on a uniaxial materials testing machine (Model 5544; Instron Corp., Canton, Mass.). The gauge length (zero load state mounted on the materials testing machine) of each specimen was measured with digital calipers (Fisher Scientific, Pittsburgh Pa.) prior to loading and used for strain measurements. Black plastic markers were affixed to the surface of each tensile specimen with cyanoacrylate prior to the application of any load. Motion of these markers was recorded using a strain video extensometer (model SVE, Instron corp., Canton, Mass.) attached to the material testing machine Video strain allowed the mechanical properties of the meniscus to be determined without concern for edge effects induced by the clamps. Each specimen was preloaded to 0.1N and cyclically preconditioned between 1N-5N for 10 cycles. Immediately following preconditioning, the specimens were loaded to failure at a rate of 10 mm/min. Load time data, strain-time data, and cross-sectional area data was combined to obtain stress-strain curves. From these curves, the tangent modulus was calculated as the slope of the linear portion of the curve. The ultimate tensile strength, ultimate load, and modulus were determined from inspection of the stress-strain curves. Mechanical properties between the intact meniscus and the meniscus scaffold were compared using a paired Student's t-test ($p<0.05$).

Results

Cellularity

Figure 5:
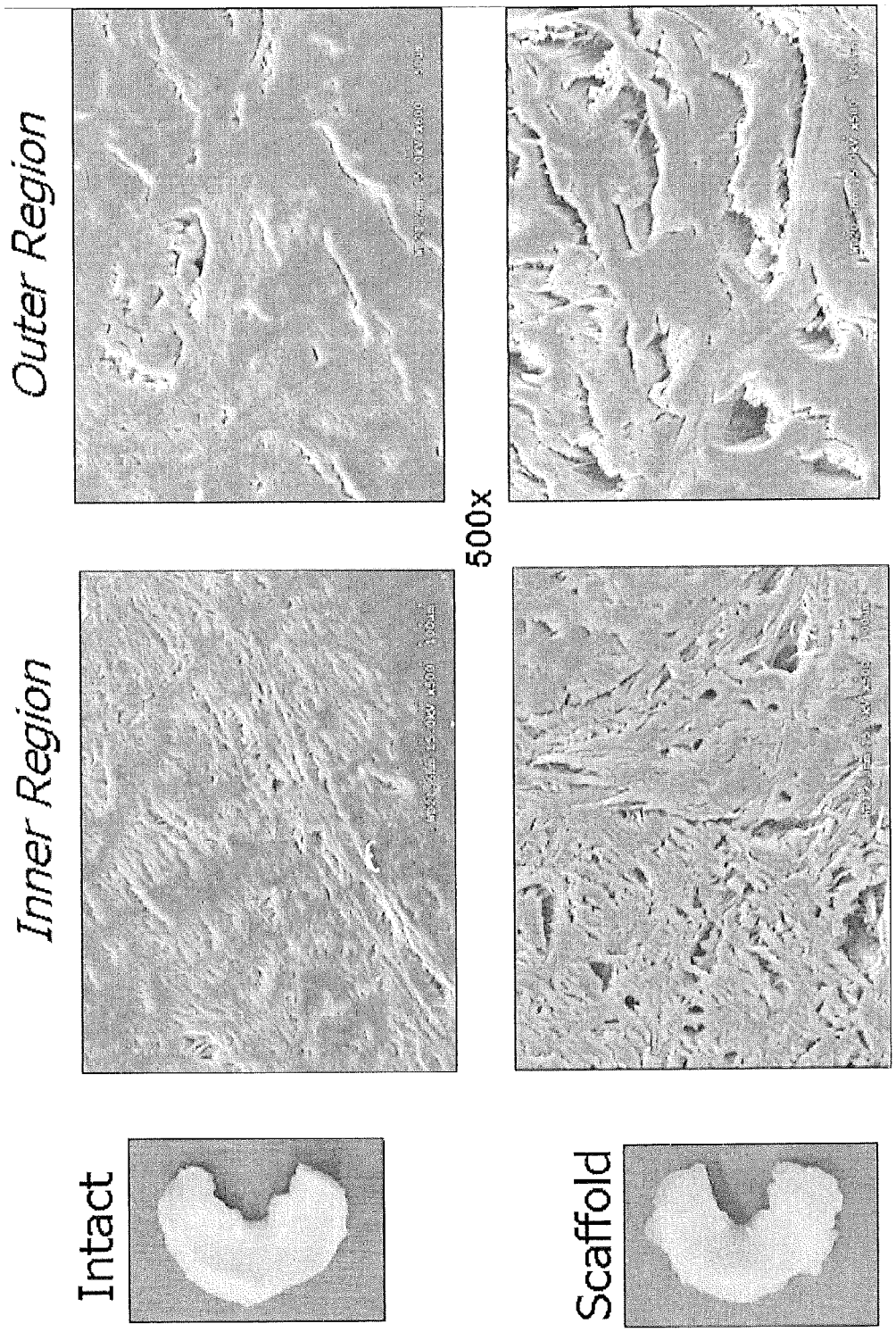
FIG. 5. Upon gross inspection, the decellularization and chemical oxidizing process did not change the general shape and architecture of the meniscus.
Figure 6:
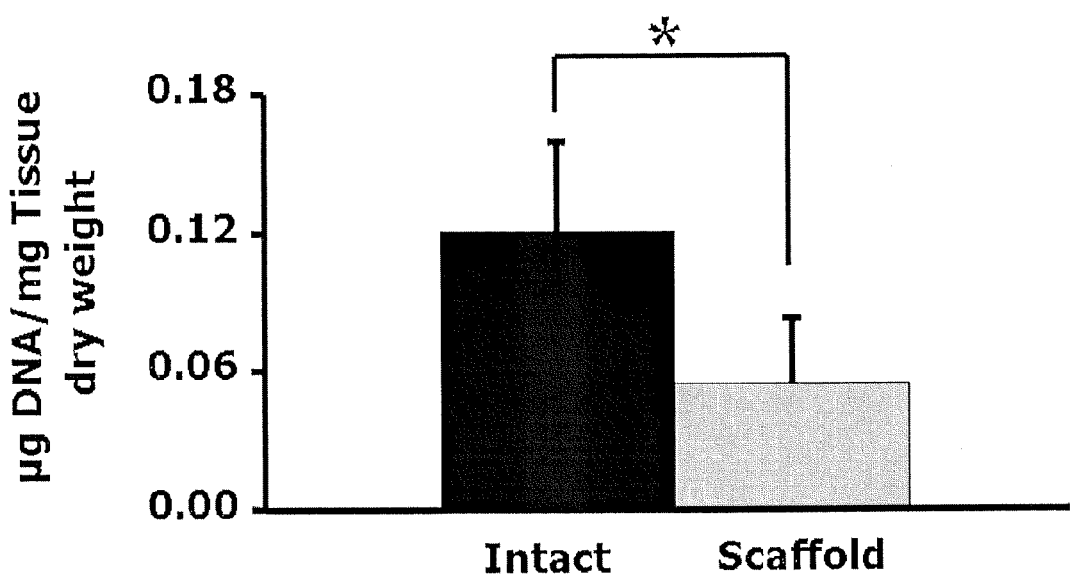
FIG. 6. DNA content analysis demonstrated a 55% decrease in DNA content in the scaffold compared to the intact meniscus ($p<0.003$).

Upon gross inspection, the decellularization and chemical oxidizing process did not change the general shape and architecture of the meniscus (FIG. 5). H&E staining showed a relative absence of nuclear staining in the scaffold compared to the intact meniscus. DAPI nuclear staining correlated with H&E staining. An abundance of nuclei in the intact meniscus and a relative absence of nuclei in the meniscus scaffold was observed. Additionally, Masson's Trichrome staining of the scaffold illustrated a similar abundance of organized collagen remaining in the meniscus scaffold when compared to the intact mensicus. The DNA content analysis demonstrated a 55% decrease in DNA content in the scaffold compared to the intact meniscus ($p<0.003$) (FIG. 6).

In Vitro Biocompatibility

For the MTS assay, the scaffold+cells had a significantly higher absorbance than latex+cells, 0.305±0.079 vs. 0.056±0.047, respectively ($p=5.41\times10^{-8}$). A statistically significant difference in absorbance of the scaffold+cells vs. cells alone (0.308±0.064) was not detected ($p=0.92$). The absorbance measured is directly proportional to the cell population metabolic activity and inversely proportional to the toxicity of the material. Therefore, cellular toxicity of the scaffold compared to cells growing in media alone was not detected. Similar results were seen in the Neutral Red assay. There was a significant difference between the scaffold+cell vs. latex+cells, 0.317±0.085 vs. 0.131±0.085 respectively ($p=3.81\times10^{-5}$). No difference between the scaffold+cells vs. cells alone (0.375±10.109) was detected ($p=0.29$). The absorbance measured is directly proportional to the cell population viability and inversely proportional to the toxicity of the material.

Porosity

Figure 7:
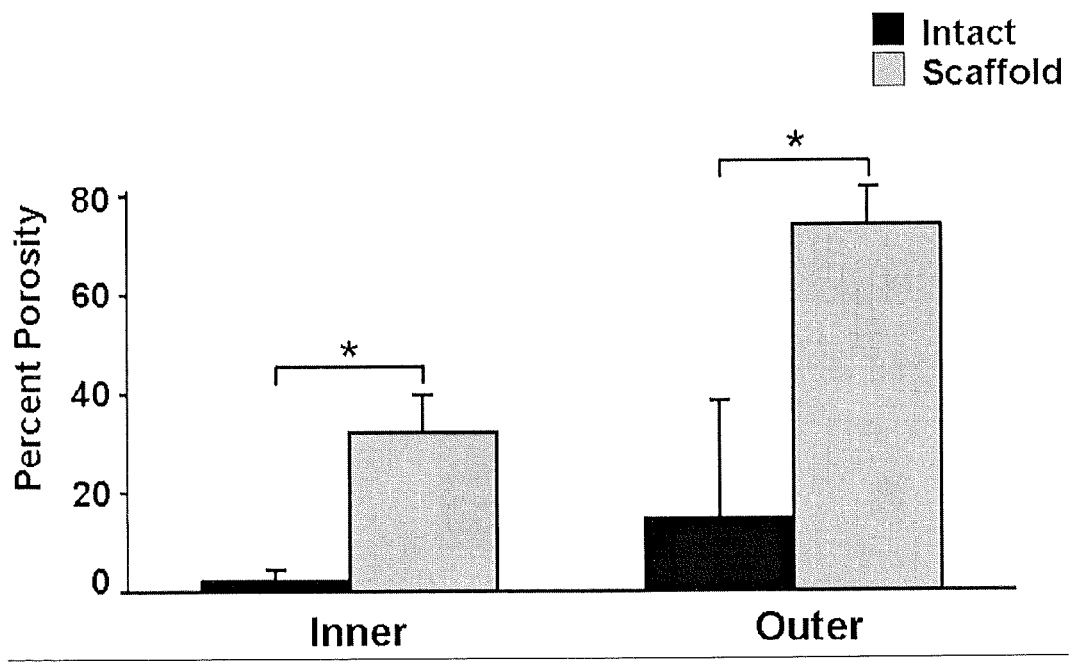
FIG. 7. Porosity measurements showed a significant difference.
Figure 8:
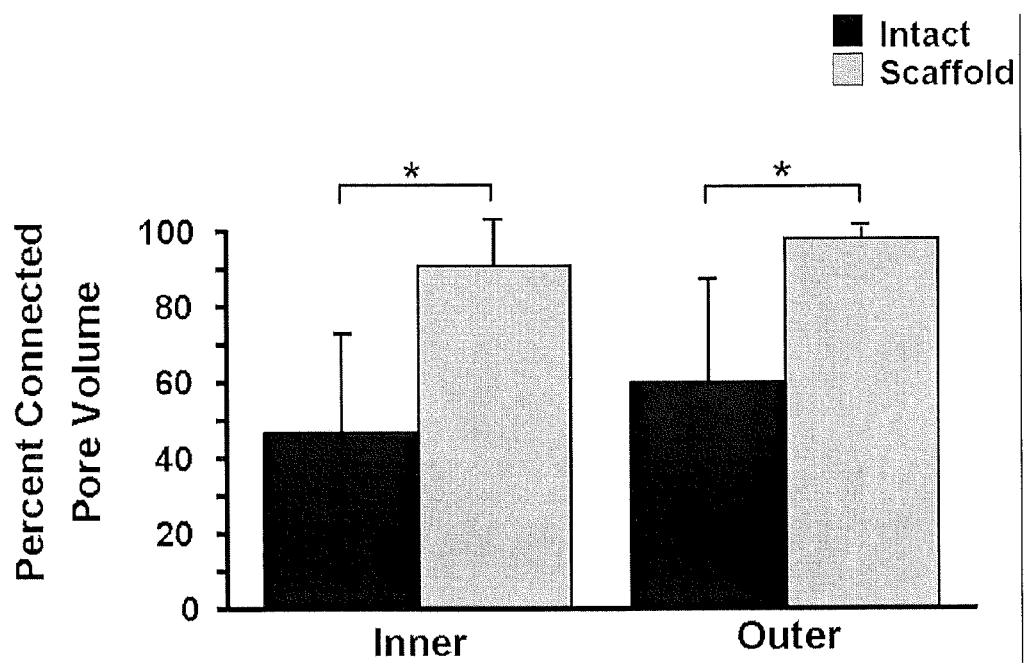
FIG. 8. Percent connected pore volume measurements showed significant differences in both inner and outer meniscus.

SEM analysis showed significant increases in pore cross-sectional area in the inner region (avascular) from 56.5 µm2 in the intact meniscus to 93.9 µm2 in the meniscus scaffold ($p=0.01$). An even greater increase in pore size was seen in the outer region (vascular), where area increased from 76.0 µm2 in the intact meniscus to 387.9 µm2 in the scaffold ($p=0.01$). MicroCT analyses demonstrated increased relative porosity from 2% to 25% in the inner region of the intact meniscus and meniscus scaffold respectively ($p=0.02$). The porosity in the outer region also increased from 15% to 74% in the intact and scaffold respectively ($p=0.001$). This is seen qualitatively and quantitatively (FIGS. 7-8). Outer region scaffold pore connectivity increased from 45% in the intact meniscus to 99% in the scaffold ($p=0.01$). Inner region scaffold pore connectivity increased from 41% in the intact meniscus to 87% in the scaffold ($p=0.009$).

Biomechanics

Figure 9:
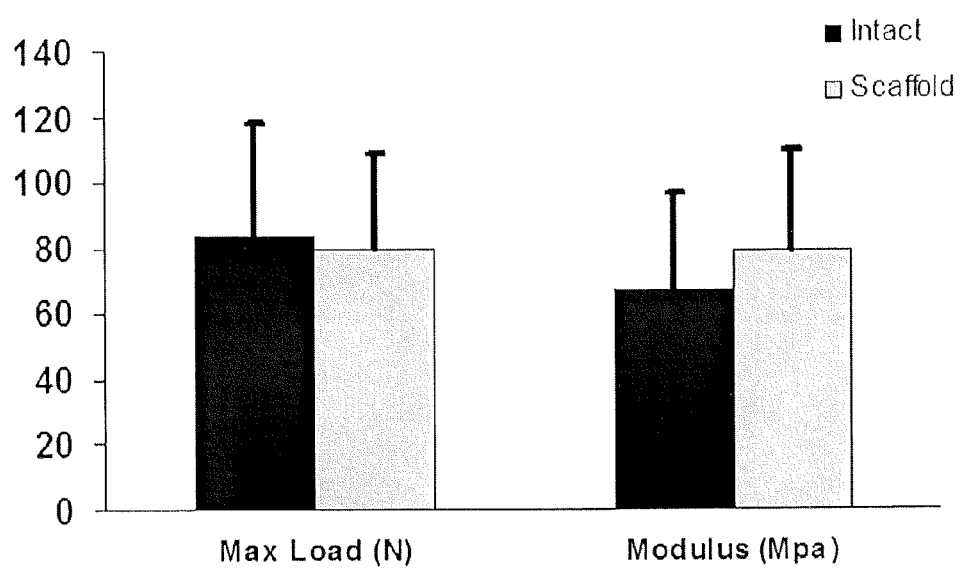
FIG. 9. Tensile testing of intact menisci and meniscus scaffolds demonstrate that ultimate load and modulus differences were not statistically significant.

The tension and compression stress-strain curves were typical for viscoelastic tissue with a characteristic toe region, linear region and failure region as shown in representative tensile curve. The compression modulus changed from 9.3±5.7 MPa in the intact meniscus to 6.8±3.0 MPa in the scaffold. This represents a 26% decrease in average elastic modulus of the meniscus scaffold compared to the intact meniscus which was not statistically significant ($p=0.42$). From tensile testing of intact menisci and meniscus scaffolds, the ultimate load and modulus showed differences that were not statistically significant (FIG. 9). The ultimate load for the intact meniscus and the scaffold was 83.4±35.3 N and 80.0±29.5 N respectively ($p=0.42$). The tangent moduli for the intact meniscus and meniscus scaffold were 67.0±29.5 MPa and 78.8±31.2 MPa, respectively ($p=0.22$).

Discussion

The ideal biological scaffold is one that is biocompatible, permeable, mechanically stable, reproducible, and readily available. The scaffold developed in this study has many of the these "ideal scaffold" attributes as shown by histology, biochemical DNA content analysis, cytotoxicity analysis, pore ultrastructural analysis, and biomechanical analysis. The histological studies illustrated the absence of cellularity in the scaffold. This was further confirmed by the DAPI nuclear staining and DNA content analysis. There was a decrease in DNA content of 55% compared to intact meniscus. As frame of reference, the meniscus scaffold has an order of magnitude less DNA than that of other clinically used FDA approved soft tissue scaffolds such as porcine small intestinal submucosa and human dermis. Residual DNA fragments (measured by DNA content assay) may remain behind in the scaffold adherent to the extracellular matrix possibly through hydrostatic forces. These fragments do not appear to comprise a defined nuclear collection as supported by absence of nuclear staining. Intuitively, an intact allograft either fresh or frozen would seem to be biocompatible. However, fresh frozen allografts have been shown to contribute to an immunologic response. This may be due to residual cellular components. The reduced cellular components in this meniscus scaffold may contribute to a decreased immunological response in vivo. However, in vivo studies are needed to investigate this hypothesis.

One could argue that a weakness of our approach is that we used allograft tissue as the foundation of our tissue engineering technology. Allograft tissue is often thought of as costly, in limited supply, and associated with disease transmission risk. Synthetic approaches may limit these drawbacks, but face the technical challenges of accurately recapitulating the biological composition and biomechanical function of the native meniscus. Allograft meniscus transplantation has been shown to be a safe and effective approach for treating symptomatic meniscus deficiency. However, the chondroprotective benefits of meniscus allograft transplantation have not been proven. We have approached this problem by starting with a tissue that closely approximates normal meniscus tissue. By modifying allograft tissue to increase its porosity, but with limited disruption to intact tissue architecture we hypothesize we will create a meniscus scaffold with improved biointegration over allograft tissue that will support improved long term clinical outcomes.

Because the meniscus scaffold in this study is made from meniscus allograft, it begins as a biocompatible substance. However, identifying any potential residual cytotoxicity may be just as important as maintaining the extracellular matrix. No significant cytotoxicity of the meniscus scaffold was observed in the in vitro Neutral Red and MTS assays. These results support the biocompatibility potential of the scaffold constructs. Future in vivo studies will further demonstrate scaffold biocompatibility and investigate potential adverse host-immune responses that are not detectable with in vitro techniques.

Porosity analysis of the intact meniscus compared to the meniscus scaffold illustrated the relative density of the intact medial meniscus structure. This may help explain why current meniscus allografts do not fully incorporate on a cellular level in vivo. By increasing the porosity and pore connectivity, a path is created for the cells to biologically incorporate throughout the entire thickness of the graft. The meniscus scaffold had greater than a 2-fold increase in porosity in both the inner and outer regions. Variability in the model analysis was minimized by analyzing all data at a constant level of threshold. The finding of increased porosity was shown in both SEM and the MicroCT data. This may potentially lead to accelerated remodeling of the graft with improved biointegration and regeneration of functional meniscus tissue that has the ability to maintain itself for longer time periods than conventional grafts.

The pores found in both the intact meniscus and meniscus scaffold were oblong. Therefore, pore size was reported in terms of cross sectional area, which better represented the pores. However, this makes comparison to existing scaffolds difficult. Additionally, ideal pore size and percent pore connectivity for biointegration in meniscus tissue is not known. Further studies will investigate the effect of pore size and connectivity with cellular migration and seeding in this allograft based meniscus scaffold.

The intact meniscus and meniscus scaffold were compared via biomechanical testing in both tension and compression. The tensile and compression data compared well with data previously published for human and bovine meniscus. We were unable to detect a statistical difference between the mechanical properties of the intact meniscus and meniscus scaffold. A subsequent statistical power analysis based on the data obtained determined that over 1600 specimens would be needed to detect a difference in ultimate tensile load. This supports that the tensile properties of the meniscus scaffold were maintained.

The compressive data appeared to show a more notable trend of diminished properties of the scaffold (although not statistically significant). This may be due to decreased tissue density of the scaffold. It may also be due to decreased resistance to fluid flow (decreased hydrostatic pressure) from increased porosity and connectivity. The tensile test results did not follow this trend. The longitudinal direction in which the tensile specimens were tested is parallel to the majority of the circumferential collagen fibers. Therefore the processing protocol may have left the circumferential fibers relatively unaffected. This would explain the little difference in the tensile mechanical properties between the meniscus scaffold and the intact meniscus. The mechanical properties of other collagen based scaffolds such as the collagen meniscus implant or porcine small intestinal submucosa based meniscus scaffold have not been shown to be comparable to the intact meniscus.

The biomechanical data in this study are supportive because a functional meniscus scaffold must maintain mechanical properties similar to the intact meniscus in order to maintain structural integrity following implantation. As with all cadaveric biomechanical studies, this does not provide a direct correlation of how the meniscus will perform in the healing environment. These data do, however give an indication of how the meniscus scaffold will perform at the time of implantation. Moreover, the results give an indication of how the processing protocol affects the mechanical integrity of extracellular matrix and suggests that the scaffold will possess initial mechanical integrity similar to that of a clinically used allograft.

The process used in this study to create the meniscus scaffold from allograft meniscus tissue results in alterations of the microarchitecture of the meniscus extracellular matrix. While any composition changes resulting from this treatment are beyond the scope of this paper, it is clear that the process is not detrimental to the in vitro biocompatibility or the biomechanical integrity of the meniscus scaffold.

A weakness of this study is that it has been performed in an animal (ovine) model and not a human knee. The benefit of the ovine model is that it allows subsequent large animal model in vivo implantation studies to be performed. Future implantation studies are needed to investigate the in vivo cell biologic ingrowth potential and functionality of this scaffold. Additionally, the ability of cells to incorporate into this meniscus scaffold compared to existing collagen based or SIS based meniscus scaffolds remains to be investigated. Future human in vitro biocompatibility and biomechanical meniscus scaffold and meniscus allograft studies are necessary to support the translation potential of this technology to clinical use.

Conclusion

In this study, a meniscus scaffold was evaluated for potential clinical application as a meniscus transplant construct in a ovine model. The data demonstrated that a decellularized meniscus scaffold with increased porosity was comparable to the intact meniscus, with an absence of in vitro cellular toxicity. While some compositional alterations of the ECM are to be expected during the processing, it is evident that many of the essential structural components remained functional with maintenance of biomechanical properties.

Example 6

Effective Cell Seeding of Meniscus Allograft Scaffold with Ovine BM-MSCs

Figure 10:
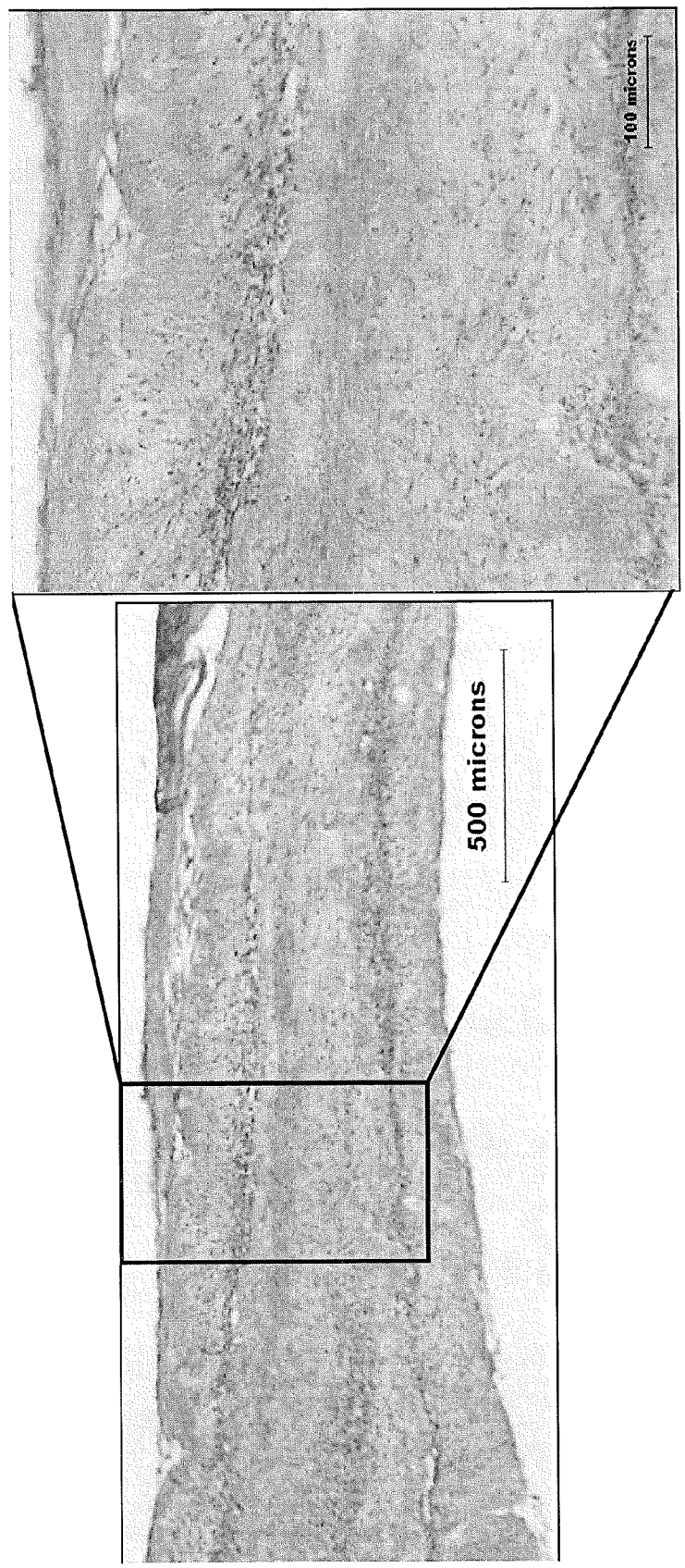
FIG. 10. Scaffold discs (2.5% PAA/2% Triton) were seeded with $1\times10^6$ BM-MSCs/ml for two weeks in static culture. Cell migration is observed over 600 μm into the scaffold.

Cell seeding experiments were performed with ovine bone marrow derived mesenchymal stem cells (BM-MSCs). Mesenchymal stem cells were isolated from bone marrow aspirates taken from the iliac crest of adult sheep as described using Percoll gradient centrifugation[1,4]. Ovine BM-MSCs were grown in α-MEM (Hyclone) supplemented with 10% FBS and 1% penicillin and streptomycin and subcultured to third passage. Verification of the MSC phenotype was achieved using flow cytometry and ovine reactive antibodies. Positive antibodies used were CD44 and vimentin and negative antibodies were von Willebrand factor and CD45[3,8,10,7]. Scaffolds were prepared using 1.5% and 2.5% peracetic acid as described above. 4 mm diameter punches were obtained at the junction of the outer and inner regions of the meniscus. The plugs were cut to a height of 2 mm to produce a scaffold disc. Cells were statically seeded onto the discs and allowed to grow for 2 and 4 weeks. Cell migration was present in the discs to a depth of greater than 600 μm in 2.5% prepared scaffolds (FIG. 10) demonstrating that the meniscus scaffold is permissive to cell seeding.

Example 7

In Vivo Implantation of Meniscus Scaffold Demonstrates Functionality in an Ovine Model Allograft (n=8), scaffold (2.5% peracetic acid/2% Triton X-100) (n=8), and scaffold constructs seeded with autologous bone marrow derived stem cells (BM-MSCs)×3 days and ×3 weeks prior to implantation were transplanted into skeletally mature sheep and harvested at 6 months post surgery.

For stem cell seeded scaffolds, BM-MSCs were harvested and cultivated as described and cultivated through passage 4 for flow cytometry analysis and scaffold seeding. Verification of the MSC phenotype was achieved using flow cytometry as described above. Cells were used for transplantation when >90% positive and <20% negative antibody staining was present. Scaffolds were seeded with $10 \times 10^6$ cells at a concentration of $1 \times 10^6$ cells/ml and cultured statically for 3 days before implantation into the cell matched sheep recipient (cell donor).

At 6 month harvest, tissue was retrieved and knees were examined. Osteoarthritis scores were collected from each joint. Average osteoarthritis scores were calculated by the Gross Assessment of Joint Changes Score published by Jackson et al., Am. J. of Sports Medicine, 1992 20:644-656. Briefly, twelve areas of the joint were assessed for the presence of osteoarthritis using the grading system reported by Jackson et al. The twelve regions assessed included the anterior medial femoral condyle, posterior medial femoral condyle, anterior lateral femoral condyle, posterior lateral femoral condyle, patella femoral groove, patella articular surface, medial tibial plateau, lateral tibial plateau, medial meniscus, lateral meniscus, presence of osteophytes, and the condyle groove junction. Each region was graded on a scale of 0 to 4. A score of 0 represented no observable gross change. A score of 1 indicated an intact surface with color changes or surface irregularities or both. A score of 2 indicated surface fibrillation or loss of cartilage with no bone exposed. A score of 3 indicated exposed bone less than 10% of the surface area in the given region. A score of 4 indicated greater than 10% bone exposed and fragmentation of cartilage around the lesion. The twelve individual scores were added together to obtain an osteoarthritis score of the joint.

Average osteoarthritis score was 10.58+/−3.96 for allograft implants, 10.63+/−4.10 for scaffold implants, and 6.86+/−2.73 for scaffold+3 day MSC seeded scaffolds, and 8.00+/−6.86 for scaffold+3 week MSC seeded scaffolds at 6 months. Lower scores correlate with lower levels of osteoarthritis (best=0, worst=48). Paired two tail student's test was run on both the 3 day seeded and 3 week seeded constructs showing significant reductions in the osteoarthritis score relative to the allograft (p=0.01 and p=0.03 respectively).

These findings support the biocompatibility and functionality of implanted scaffolds and constructs described herein as compared to allograft, and particularly support the potential of stem cell seeded scaffolds prepared using these methods to limit the progression of osteoarthritis.

Catastrophic failure of the scaffolds and seeded constructs has not been observed, but incomplete healing of the posterior horn region in all groups was observed. More detailed analysis of the surgical groups, including histology/immunohistochemistry, qRTPCR, and biomechanical testing is in progress.

Figure 11:
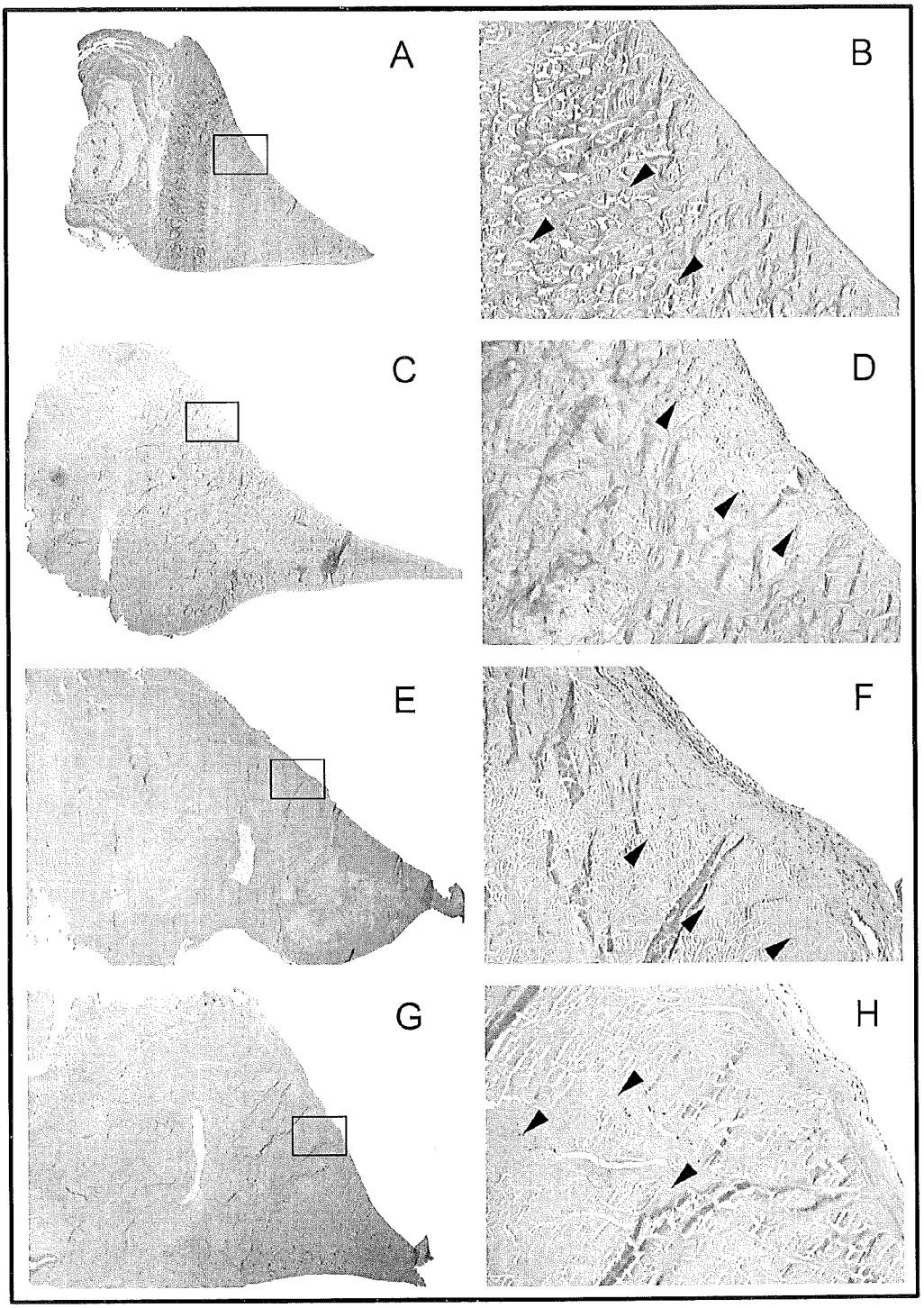
FIG. 11. Low and high (10×) power images showing H&E staining of coronal sections taken of (A, B) normal adult ovine medial meniscus tissue; and medial meniscus transplants harvested at 6 months following implantation. Harvested transplants include (C, D) allograft; (E, F) scaffold; and (G, H) scaffold seeded with BM-MSCs×3 days. Boxes depict location of 10× image. Arrows depict cell localization.

FIG. 11 presents histology (1.25× and 10×) of normal meniscus (A, B); allograft (C, D); scaffold (E, F); scaffold+3 day seeded MSC (G, H). Normal meniscus tissue demonstrates diffuse cellularity throughout the substance of the meniscus (B). Allograft transplants demonstrate a monolayer of cells at the surface of the meniscus with limited cellular penetration into the substance of the meniscus, consistent with published research (D) (Kuhn et al., Allograft meniscus transplantation. *Clin Sports Med,* 15 (3): 537-6, 1996; Rodeo et al., Histological analysis of human meniscal allografts. A preliminary report. *J Bone Joint Surg Am,* 82-A(8): 1071-82. 2000). Empty scaffold implants demonstrate a monolayer of cells at the surface of the meniscus similar to the allograft implant, also with limited cellular penetration (E). MSC-seeded constructs demonstrate deeper cellular penetration of cells toward the central substance of the scaffold (F). All transplanted tissues (C-F) have less abundant cellularity than native tissue, supporting the need to improve the biointegration potential and cellular penetration of tissue engineered constructs prior to implantation.

Example 8

Meniscus scaffolds are prepared by the following protocol. Menisci are sterilely harvested from the knee joint. All decellularization solutions and containers are sterile for the entire process.

Each menisci is placed into 500 mL of deionized water and placed on a shaker at 200 RPM and 37° C. for 24 hours. The water solution is replaced every 24 hours for 2 days.

On the third day, the water is replaced with 500 mL of 0.05% Trypsin EDTA (Gibco) and placed back on the shaker for 24 hours.

The Trypsin is then replaced with 500 mL DMEM High Glucose supplemented with 1% antibiotic/antimitotic and 10% FBS and placed back on the shaker for 24 hours.

The DMEM solution is then replaced with 2.5% peracetic acid and 2% Triton X-100 in deionized water for 24 hours on the shaker.

The acid solution is then replaced and placed on the shaker for an additional 24 hours. (48 hour total acid treatment)

The acid is then washed off the scaffold with deionized water for 1 hour on the shaker followed by 2 days of washing with water changes every 24 hours. Residual peracetic acid is detected using testing strips. Washing is continued until no residual peracetic acid is detected. Typically, 48 hours of water washes are needed to remove residual traces of peracetic acid.

The foregoing is illustrative of the present invention, and is not to be construed as limiting thereof. The invention is defined by the following claims, with equivalents of the claims to be included therein.

That which is claimed is:

1. A method of producing a meniscus scaffold comprising:
   decellularizing a meniscus tissue with an oxidant and detergent simultaneously to remove extraneous material and increase the pore size and porosity therein;
   seeding the tissue with allogeneic or autogeneic cells; and then,
   applying mechanical stress to the tissue in a bioreactor system, wherein said mechanical stress comprises compression;
   to thereby produce said meniscus scaffold.

2. The method of claim 1, wherein said oxidant is hydrogen peroxide, peracetic acid, or a mixture thereof.

3. The method of claim 1, wherein said oxidant is in an aqueous solution at a concentration of between 0.5 and 7% (w/v).

4. The method of claim 1, wherein said oxidant is in an aqueous solution at a concentration of between 1 and 4% (w/v).

5. The method of claim 1, wherein said detergent is in an aqueous solution at a concentration of between 0.5 and 5%.

6. The method of claim 1, wherein said detergent is in an aqueous solution at a concentration of between 1 and 3%.

7. The method of claim 1, wherein said cells are autologous cells.

8. The method of claim 1, wherein said cells are mesenchymal stem cells or adipose stem cells.

9. The method of claim 1, further comprising growing the cells under hypoxic conditions.

10. The method of claim 1, further comprising growing the cells in an oxygen tension from 0 to 10%.

11. The method of claim 1, wherein said mechanical stress is compression of up to 10%.

12. The method of claim 11, wherein said compression is cyclically or periodically applied.

13. The method of claim 1, wherein said meniscus tissue is mammalian.

14. The method of claim 1, wherein said meniscus tissue is human.

15. The method of claim 1, further comprising exposing said cells to one or more growth factors selected from FGF-2, GDF-5 and TGF-$\beta$1 in said bioreactor system.

* * * * *

UNITED STATES PATENT AND TRADEMARK OFFICE
CERTIFICATE OF CORRECTION

PATENT NO. : 8,906,362 B2
APPLICATION NO. : 13/258490
DATED : December 9, 2014
INVENTOR(S) : Ferguson et al.

It is certified that error appears in the above-identified patent and that said Letters Patent is hereby corrected as shown below:

In the Specification
Column 1, Line 14: Please insert the following heading and paragraph before the heading
"FIELD OF THE INVENTION":

-- STATEMENT OF GOVERNMENT SUPPORT
This invention was made with Government support under contract number 1K08AR059172-01 awarded by the National Institutes of Health. The Government has certain rights in the invention. --

Column 16, Line 15: Please correct "(0.375±10.109) was detected"
to read -- (0.375±0.109) was detected --

Signed and Sealed this
Twenty-eighth Day of April, 2015

Michelle K. Lee
*Director of the United States Patent and Trademark Office*